US012004832B2

(12) United States Patent
Waterbury et al.

(10) Patent No.: US 12,004,832 B2
(45) Date of Patent: Jun. 11, 2024

(54) ROTATABLE CARRIAGE FOR AN INSTRUMENT HOLDER

(71) Applicant: INTUITIVE SURGICAL OPERATIONS, INC., Sunnyvale, CA (US)

(72) Inventors: Andrew Cullen Waterbury, Santa Clara, CA (US); Daniel H. Gomez, Los Gatos, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 231 days.

(21) Appl. No.: 17/444,166

(22) Filed: Jul. 30, 2021

(65) Prior Publication Data
US 2022/0039892 A1 Feb. 10, 2022

Related U.S. Application Data

(60) Provisional application No. 63/063,193, filed on Aug. 7, 2020.

(51) Int. Cl.
| | | |
|---|---|---|
| *B25J 9/04* | (2006.01) | |
| *A61B 34/00* | (2016.01) | |
| *A61B 34/35* | (2016.01) | |
| *B25J 5/00* | (2006.01) | |

(52) U.S. Cl.
CPC .............. *A61B 34/70* (2016.02); *A61B 34/35* (2016.02); *B25J 5/005* (2013.01); *B25J 9/04* (2013.01)

(58) Field of Classification Search
CPC .. B25J 5/005; B25J 9/04; A61B 34/35; A61B 34/70
See application file for complete search history.

(56) References Cited

U.S. PATENT DOCUMENTS

| | | | | |
|---|---|---|---|---|
| 1,002,236 | A | * | 9/1911 | Dumont .................. F16H 55/06 74/439 |
| 3,319,413 | A | * | 5/1967 | Costner .................. D01H 1/242 74/450 |
| 11,109,926 | B2 | | 9/2021 | Seow et al. |
| 2015/0090057 | A1 | * | 4/2015 | Pacheco .................. F16H 19/02 74/25 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — William C Joyce
(74) *Attorney, Agent, or Firm* — JONES ROBB, PLLC

(57) ABSTRACT

An instrument holder generally includes a carriage support having an output drive and a carriage configured to removably couple an instrument thereto, the carriage may have a lateral opening extending radially outward from a central axis of the carriage, and the lateral opening may be configured to receive a portion of the instrument therein. The carriage may further include a positioning member disposed on an outer surface of the such that rotation of the output drive changes an angular position of the carriage relative to the carriage support. The positioning member may be configured to allow the output drive to operably couple with the carriage at an engagement point adjacent to the lateral opening. The carriage may include a positionable door or a fin extending into the lateral opening to allow the output drive to drive the carriage around a full 360 degree rotation or greater.

22 Claims, 9 Drawing Sheets

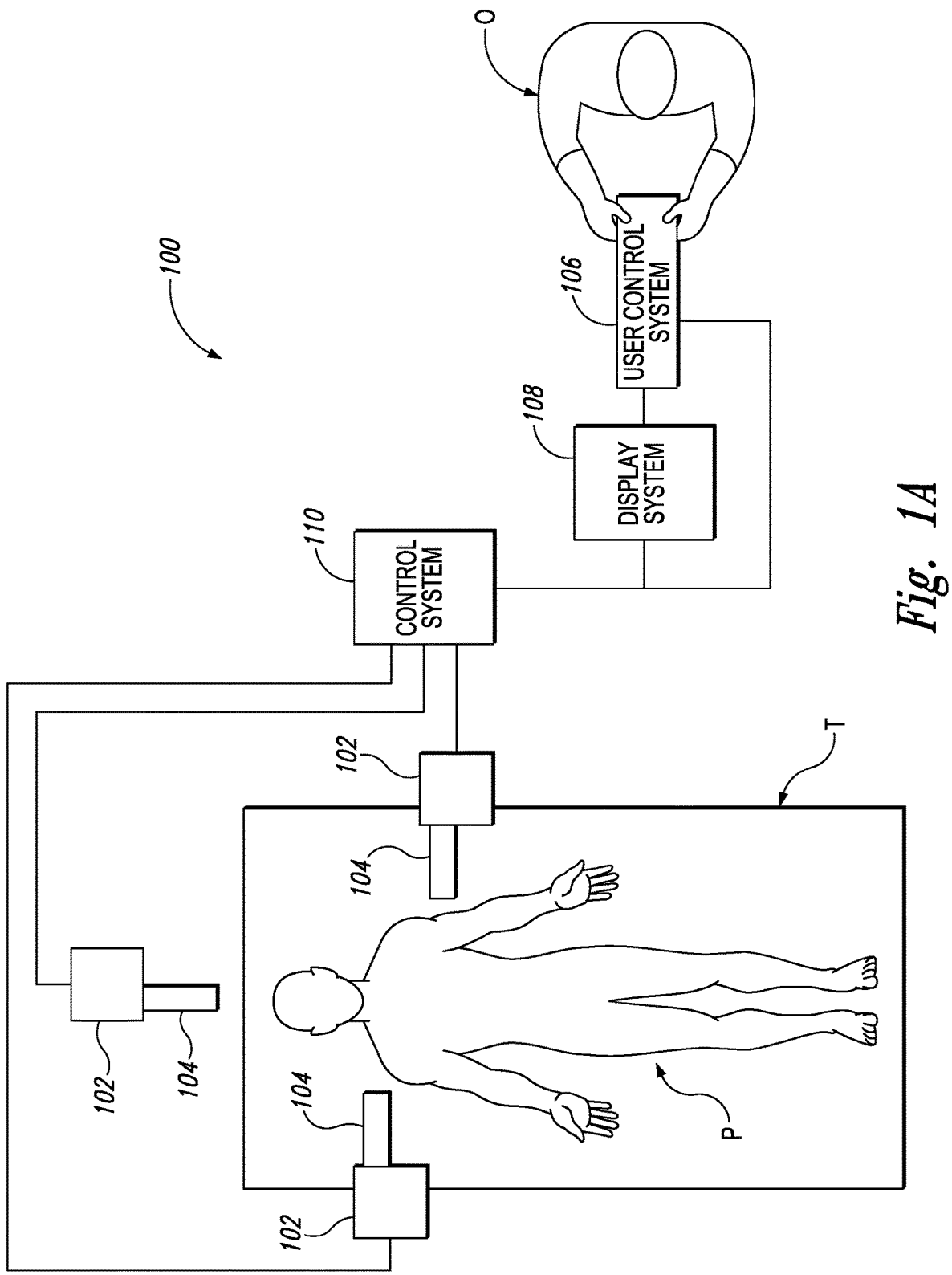

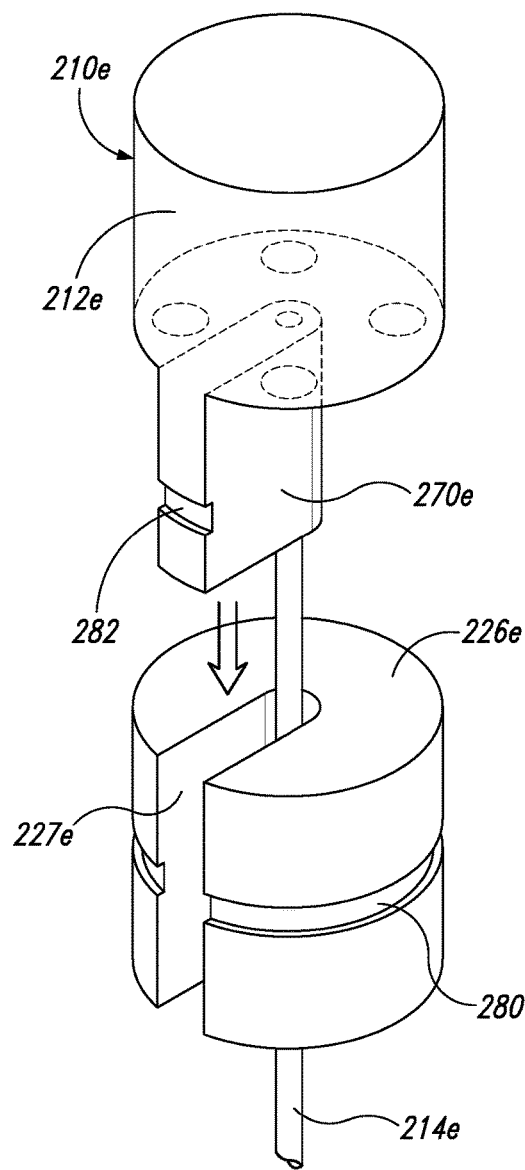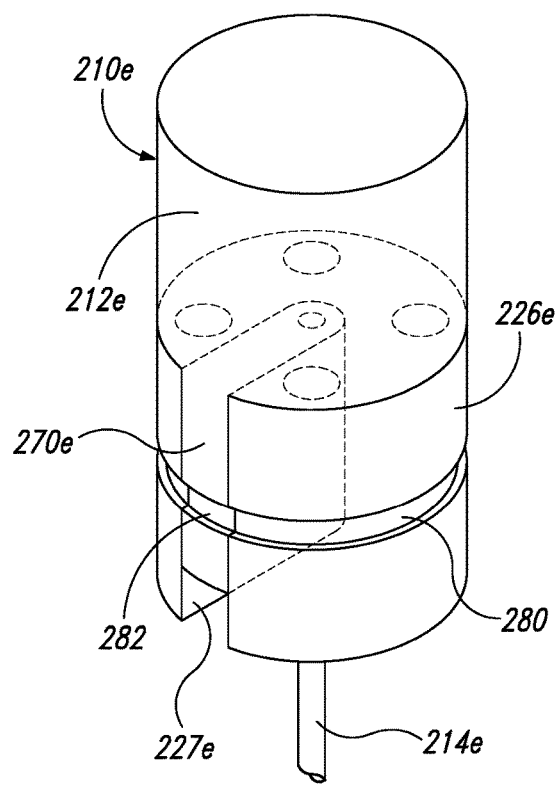
*Fig. 7A*  *Fig. 7B*

ROTATABLE CARRIAGE FOR AN INSTRUMENT HOLDER

CROSS REFERENCE TO RELATED APPLICATION

This application claims the benefit under 35 U.S.C. § 119(e) of U.S. Provisional Application No. 63/063,193, filed Aug. 7, 2020, entitled "Rotatable Carriage For An Instrument Holder," which is hereby incorporated by reference for all purposes in its entirety.

TECHNICAL FIELD

Aspects of the present disclosure generally relate to devices and methods for performing a computer-assisted teleoperated procedure and, more specifically, to devices for transferring degrees of freedom to a tool.

BACKGROUND

Minimally invasive medical techniques are intended to reduce an amount of tissue that is damaged during medical procedures, thereby reducing patient recovery time, discomfort, and harmful side effects. Such minimally invasive techniques may be performed through natural orifices in a patient anatomy or through one or more surgical incisions. An operator (e.g., a physician) may insert minimally invasive medical instruments (surgical, diagnostic, therapeutic, biopsy instruments, etc.) through these natural orifices or incisions to reach a target tissue location. Robotic medical systems allow a user to control such medical instruments via a manipulator to which the instrument is mounted. One such minimally invasive technique is to move one or more instruments to a region of interest within the patient anatomy to perform a medical procedure. Control of such a manipulator assembly by an operator involves the management of several degrees of freedom including at least the management of insertion, retraction, and roll of the instrument with respect to the patient anatomy, as well as articulation of an instrument end effector.

Minimally invasive telesurgical systems allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments.

Communication signals may be transmitted between components of a robotic medical system using various cables, including optical fibers, coaxial conductors, copper conductors, twisted wire pairs, etc. When using such communication cables on articulating medical instruments, it is desirable to reduce friction and stress on the internal components of the cable to extend the cable life. Twisting a wrapped cable can impart an unwrap torque, shifting any tensile load disproportionately to the inner wrap and/or core of the cable and significantly reduce cable life. Loading of the cable and articulation of the end effector can further contribute to the unwrap torque. Further, the tension and effective stiffness changes in the cable at different twisted states influencing the drivetrain friction, which can adversely affect the consistency of movement of the medical instrument during use.

SUMMARY

In accordance with embodiments of the present disclosure, an apparatus is provided. The apparatus generally includes a carriage support having an output drive and a carriage configured to removably couple an instrument thereto. The carriage may have a lateral opening extending radially outward from a central axis of the carriage and extending between a proximal end portion and a distal end portion of the carriage, and the lateral opening may be configured to receive a portion of the instrument therein. The apparatus may also include a positioning member disposed on an outer surface of the carriage and operably coupled with the output drive such that rotation of the output drive changes an angular position of the carriage relative to the carriage support. The positioning member may be configured to allow the output drive to operably couple with the carriage at an engagement point adjacent to the lateral opening.

In accordance with embodiments of the present disclosure, a manipulator arm for articulating an instrument is provided. The manipulator arm may generally include a plurality of joints and links and an instrument holder configured to couple the plurality of joints and links to the instrument. The instrument holder may include a base member coupled to the manipulator arm and a carriage configured to releasably attach to the instrument and drive the instrument. The carriage may include a central axis and a lateral opening extending radially outward from central axis, where the lateral opening may be configured to receive a portion of the instrument in a direction substantially perpendicular to the central axis. The carriage may further include a positioning member positionable adjacent the lateral opening such that, during operation, the carriage is rotatable with respect to the base member about the central axis to an angular extent such that a portion of the carriage containing the lateral opening is configured to rotate past a contact point with the base member.

In accordance with any of the embodiments disclosed herein, the carriage support may be configured to translate the carriage along an instrument holder base member of an instrument holder.

In accordance with any of the embodiments disclosed herein, rotation of the carriage may cause a shaft roll of the instrument when coupled to the carriage.

In accordance with any of the embodiments disclosed herein, the output drive may comprise gear teeth.

In accordance with any of the embodiments disclosed herein, the positioning member may comprise gear teeth circumferentially arranged along an outer surface of the carriage.

In accordance with any of the embodiments disclosed herein, the gear teeth of the positioning member may be circumferentially arranged along a distal end surface of the carriage.

In accordance with any of the embodiments disclosed herein, the gear teeth of the positioning member may be circumferentially arranged along an outer surface of the carriage between the proximal end portion and the distal end portion of the carriage.

In accordance with any of the embodiments disclosed herein, the apparatus may further include a positionable door rotatably coupled to a first edge of the lateral opening. The positionable door may be rotatably movable between a first position wherein the positionable door allows a shaft of the instrument to enter the lateral opening, and a second position wherein the positionable door abuts a second edge of the lateral opening opposite the first edge.

In accordance with any of the embodiments disclosed herein, the positionable door may comprise gear teeth that align with the gear teeth of the positioning member in the second position of the positionable door to form a continuous loop of gear teeth around the carriage such that the output drive of the carriage support can operably couple with the carriage around an entire circumference of the carriage.

In accordance with any of the embodiments disclosed herein, the positionable door may project outward from an outer surface of the carriage in the first position, and may be further rotatably movable to a third position wherein the positionable door projects into the lateral opening of the carriage.

In accordance with any of the embodiments disclosed herein, the positionable door may have a lock to fix the positionable door in the second position.

In accordance with any of the embodiments disclosed herein, the positioning member may be removable from the carriage.

In accordance with any of the embodiments disclosed herein, the gear teeth of the positioning member may be positioned on a track extending around the outer surface of the carriage, may further comprise a curved track guide extending away from the output drive, and the curved track guide may be configured to interface with the track of the carriage to support the carriage as the output drive changes the angular position of the carriage.

In accordance with any of the embodiments disclosed herein, an arc length of the curved track guide may be longer than a width of the lateral opening such that the curved track guide is configured to extend across the lateral opening and engage with a portion of the track on an opposite side of the lateral opening.

In accordance with any of the embodiments disclosed herein, an axial drive element may be operably coupled to an axial transmission member extending to the carriage support and a rotational drive element may be operably coupled to a rotational transmission member extending to the carriage support. The axial drive element may be configured to axially position the carriage support with respect to the instrument holder base member, and the rotational drive element may be configured to angularly position the carriage with respect to the carriage support by rotating the output drive.

In accordance with any of the embodiments disclosed herein, the axial transmission member may be a drive shaft, a belt, or a cable.

In accordance with any of the embodiments disclosed herein, the rotational transmission member may be a drive shaft, a belt, or a cable.

In accordance with any of the embodiments disclosed herein, a proximal surface of the carriage may be configured to couple a distal end portion of an instrument housing with an instrument shaft extending through the lateral opening.

In accordance with any of the embodiments disclosed herein, the apparatus may further include the instrument, the positioning member may comprise a fin projecting from the instrument, and the lateral opening may be configured to receive the fin.

In accordance with any of the embodiments disclosed herein, the fin may comprise gear teeth that align with the gear teeth of the positioning member when the instrument is coupled to the carriage, and the gear teeth of the fin and the gear teeth of the positioning member may form a continuous loop of gear teeth around the carriage such that the output drive can engage with the carriage around an entire circumference of the carriage.

In accordance with any of the embodiments disclosed herein, the fin may be removable from the instrument.

DESCRIPTION OF THE DRAWINGS

Many aspects of the present disclosure can be better understood with reference to the detailed description along with the following drawings. The components in the drawings are not necessarily drawn to scale. Instead, emphasis is placed on illustrating clearly the principles of the present disclosure. Furthermore, components can be shown as transparent in certain views for clarity of illustration only and not to indicate that the component is necessarily transparent. Components may also be shown schematically.

FIG. 1A is a simplified diagram of a medical system configured in accordance with an embodiment of the present disclosure.

FIGS. 7A and 7B are perspective detail views of a portion of the instrument holder and medical instrument assembly of FIGS. 2A and 2B, showing a rotatable carriage and a medical instrument in a disassembled configuration (FIG. 7A) and an assembled configuration (FIG. 7B).

In the specification, it should be appreciated that like reference numerals are used to identify like elements illustrated in one or more of the figures for purposes of illustrating embodiments of the present disclosure and not for purposes of limiting the same.

DETAILED DESCRIPTION

Figure 1B:
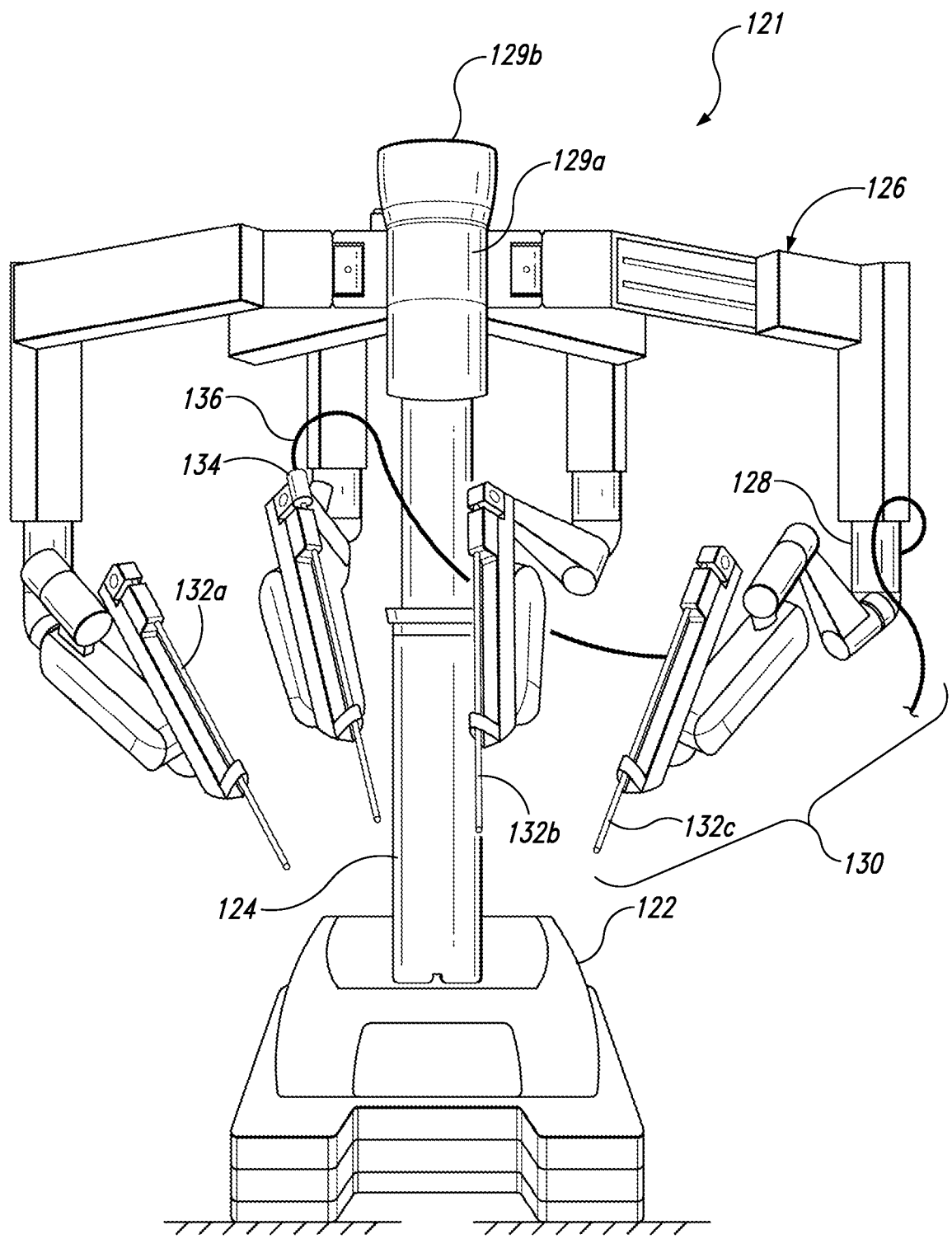
FIG. 1B is a perspective view of a structural representation of the medical system of FIG. 1A.

The present disclosure generally relates to an instrument holder for a robotic medical system, the instrument holder having a rotatable carriage for carrying and rotating a medical instrument. The systems described herein are designed to extend instrument cable life by rotating the rotatable carriage to roll the medical instrument, rather than rotating the shaft of the instrument relative to other components of the instrument. Various medical systems may include communication cables on one or more modular medical instruments. Embodiments of the present disclosure reduce stress and friction on the internal components of the instrument and instrument cable to extend the cable life. Using a rotatable carriage to roll the medical instrument can minimize unwrap torque on the instrument cable, reducing tensile load on the inner wrap and/or core of the cable. By rolling the rotatable carriage, the cable tension and stiffness is consistent, reducing variations in the friction of the drivetrain such that movement of the medical instrument during use can be more precise. In configurations where an instrument is mounted to a proximal end portion of a rotatable carriage, a lateral opening (e.g., a slot) may extend into the rotatable carriage to aid with mounting of the instrument, such that an instrument shaft can pass through the rotatable carriage toward the surgical field. However, the slot may interfere with a maximum potential rotation range of the rotatable carriage, and therefore limit the rotational range of the instrument, by causing disengagement of a drive gear from gear teeth positioned on the rotatable carriage. Similarly, the slot may cause disengagement of a support or bearing configuration for the rotation of the carriage. In this regard, it may be desirable to configure the rotatable carriage such that engagement of the drive gear is extended to the edges of the slot and/or past the slot to increase the rotation range of the rotatable carriage and the instrument.

The present disclosure describes various instruments and portions of instruments in terms of their state in three-dimensional space. As used herein, the term position refers to the location of an object or a portion of an object in a three-dimensional space (e.g., three degrees of translational freedom along Cartesian X-, Y-, and Z-coordinates). As used herein, the term orientation refers to the rotational placement of an object or a portion of an object (e.g., three degrees of rotational freedom, such as roll, pitch, and yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object. Further, as used herein, the term "distal" means a location closer to a surgical site and the term "proximal" means a location farther away from the surgical site, unless otherwise indicated.

FIG. 1A is a simplified diagram of a medical system ("system 100"). In some embodiments, the system 100 may be suitable for use in, for example, surgical, teleoperated surgical, diagnostic, therapeutic, or biopsy procedures. While some embodiments are provided herein with respect to such procedures, any reference to medical or surgical instruments and medical or surgical methods is intended as non-limiting. The systems, instruments, and methods described herein may be used for animals, human cadavers, animal cadavers, portions of human or animal anatomy, nonsurgical diagnosis, as well as for industrial systems and general robotic, general teleoperational, or robotic medical systems. For example, the systems and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical medical treatment or diagnosis procedures.

As shown in FIG. 1A, the system 100 generally includes a plurality of manipulator assemblies 102 (having one or more drive elements). Although three manipulator assemblies 102 are illustrated in the embodiment of FIG. 1A, in other embodiments, more or fewer manipulator assemblies may be used. The exact number of manipulator assemblies will depend on the medical procedure and the space constraints within the operating room, among other factors. Multiple user control systems 106 may be co-located or they may be positioned in separate locations. Multiple user control systems 106 allow more than one operator to control one or more teleoperated manipulator assemblies in various combinations.

The manipulator assembly 102 is used to operate a medical instrument 104 (e.g., a surgical instrument or an image capturing device) in performing various procedures on a patient P. The medical instrument 104 may be sterile prior to being used in the various procedures. The manipulator assembly 102 may be teleoperated, non-teleoperated, or a hybrid teleoperated and non-teleoperated assembly with select degrees of freedom of motion that may be motorized and/or teleoperated, and select degrees of freedom of motion that may be non-motorized and/or non-teleoperated. In some embodiments, the manipulator assembly 102 may be mounted near an operating or surgical table T, or the manipulator assembly 102 may be mounted directly to the table T or to a rail coupled to the table T. In various other embodiments, the manipulator assembly 102 may be mounted to a manipulating system (e.g., a patient-side cart). The manipulating system may be separate from and spaced from the table T in the operating room and may be independently movable relative to the table T.

The manipulator assembly 102 may be mounted to a ceiling, floor, and/or wall of the operating room. In embodiments in which a plurality of manipulator assemblies 102 are employed, one or more of the manipulator assemblies 102 may support surgical instruments, and another of the manipulator assemblies may support an image capturing device such as a monoscopic or stereoscopic endoscope. In such embodiments, one or more of the manipulator assemblies 102 may be mounted to any structure or in any manner as described above. For example, one manipulator assembly 102 may be mounted to the table T and another manipulator assembly 102 may be mounted to a manipulating system.

A user control system 106 allows an operator (e.g., a surgeon or other clinician, as illustrated in FIG. 1A) to view the interventional site and to control the manipulator assembly 102. In some examples, the user control system 106 is a surgeon console, which can be located in the same room as the operating or surgical table T, such as at the side of a table on which the patient P is located. However, the operator O can be located in a different room or a completely different building from patient P. The user control system 106 generally includes one or more input devices for controlling the manipulator assembly 102. The input devices may include any number of a variety of devices, such as joysticks, trackballs, data gloves, trigger-guns, hand-operated controllers, voice recognition devices, body motion or presence sensors, and/or the like. The input devices may be provided with the same degrees of freedom as the associated medical instrument 104 to provide the operator O a strong sense of directly controlling the medical instrument 104. In this regard, the input devices may provide the operator O with telepresence: the perception that the input devices are integral with medical instrument 104.

The input devices may have more or fewer degrees of freedom than the associated medical instrument 104 and still provide the operator O with telepresence. The input devices may optionally be manual input devices that move with six degrees of freedom, and may also include an actuatable handle for actuating instruments (for example, for closing grasping jaws, applying an electrical potential to an electrode, delivering a medicinal treatment, etc.).

The manipulator assembly 102 may support the medical instrument 104 and may include a kinematic structure of one or more non-servo controlled links (e.g., a manipulator support structure having one or more links that are manually positioned and locked in place), and/or one or more servo controlled links (e.g., one or more links that are controlled in response to commands from a control system), and an instrument holder. The manipulator assembly 102 may optionally include a plurality of actuators or motors that drive inputs on the medical instrument 104 in response to commands from the control system (e.g., a control system 110). The actuators may optionally include drive systems that when coupled to the medical instrument 104 may advance the medical instrument 104 into a naturally or surgically created anatomic orifice.

Other drive systems may move the distal end of the medical instrument 104 in multiple degrees of freedom, which can include three degrees of linear motion (e.g., linear motion along the X, Y, Z Cartesian axes), and three degrees of rotational motion (e.g., rotation about the X, Y, Z Cartesian axes). Additionally, the actuators can be used to actuate an articulable end effector of the medical instrument 104, e.g., for grasping tissue in the jaws of a biopsy device. Actuator position sensors such as resolvers, encoders, potentiometers, and other mechanisms may provide sensor data to the system 100 describing the rotation and orientation of the shafts of the actuator. Such position sensor data may be used to determine motion of the objects manipulated by the actuators. The manipulator assembly 102 may position its held instrument such that a pivot point occurs at the entry aperture into the patient. The manipulator assembly 102 may then manipulate its held instrument so that the instrument may be pivoted about the pivot point, inserted into and retracted out of the entry aperture, and/or rotated about its shaft axis.

The system 100 may also include a display system 108 for displaying an image or representation of the surgical site and the medical instrument 104. The display system 108 and the user control system 106 may be oriented so the operator O can control the medical instrument 104 and the user control system 106 with the perception of telepresence. The medical instrument 104 may include a visualization system, which may include a viewing scope assembly that records a concurrent or real-time image of a surgical site and provides the image to the operator O and/or other operators or personnel through one or more displays of the system 100, such as one or more displays of the display system 108. The concurrent image may be, for example, a two- or three-dimensional image captured by an endoscope positioned within the surgical site. The visualization system may be implemented as hardware, firmware, software, or a combination thereof that interact with or are otherwise executed by one or more computer processors that may include the processors of the control system 110. The display system 108 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including, e.g., time-based or velocity-based information) images, and/or as images from models created from the pre-operative or intra-operative image data sets.

The system 100 may also include the control system 110. The control system 110 may include at least one memory (not shown) and at least one computer processor (not shown) for effecting control between the medical instrument 104, the user control system 106, and the display system 108. The control system 110 also includes programmed instructions (e.g., a non-transitory machine-readable medium storing the instructions) to implement some or all the methods described in accordance with aspects of the present disclosure disclosed herein, including instructions for providing information to the display system 108. While the control system 110 is shown as a single block in the simplified schematic of FIG. 1A, the system may include two or more data processing circuits with one portion of the processing optionally being performed on or adjacent to the manipulator assembly 102, another portion of the processing being performed at the user control system 106, etc. The processors of the control system 110 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the robotic medical systems described herein. In one embodiment, the control system 110 supports wireless communication protocols such as Bluetooth, IrDA, HomeRF, IEEE 802.11, DECT, and Wireless Telemetry.

Movement of the manipulator assembly 102 may be controlled by the control system 110 such that a shaft or intermediate portion of instruments mounted to the manipulator assemblies 102 are constrained to safe motions through minimally invasive surgical access sites or other apertures. Such motion may include, for example, axial insertion of a shaft through an aperture site, rotation of the shaft about its axis, and pivotal motion of the shaft about a pivot point adjacent the access site. In some cases, the risk of excessive lateral motion of the shaft that might potentially cause hazardous forces on the tissues adjacent the aperture or enlarge the access site inadvertently is inhibited. Some or all of such constraint on the motions of the manipulator assemblies 102 at the access sites may be imposed using mechanical manipulator joint linkages that inhibit improper motions, or may in part or in full be imposed using data processing and control techniques. In some embodiments, the control system 110 may receive force and/or torque feedback from the medical instrument 104. Responsive to the feedback, the control system 110 may transmit signals to the user control system 106. In some examples, the control system 110 may transmit signals instructing one or more actuators of the manipulator assembly 102 to move the medical instrument 104.

FIG. 1B is a perspective view of one embodiment of a manipulating system 121 configured in the form of a cart that is located near the patient during a medical procedure. The teleoperational assembly of FIG. 1B may also be referred to as a patient side cart. The manipulating system 121 generally allows manipulation of three medical instruments 132a, 132b, 132c (e.g., the medical instrument 104 of FIG. 1A), and a medical tool 134 that may include an imaging device, such as a stereoscopic endoscope used for the capture of images of the work piece or of the site of the procedure (a "work site"). The medical tool 134 may transmit signals over a cable 136 to a control system (e.g., the control system 110 of FIG. 1A). Manipulation may be provided by robotic manipulators 126 having a number of links that are coupled together and manipulated through joints and a manipulator arm portion 130. The medical instruments 132a, 132b, and 132c, and the medical tool 134 can be positioned and manipulated through natural orifices or incisions in the patient so that a kinematic remote center is maintained at the incisions or natural orifices. Images of the work site can include images of the distal end portions of the medical instruments 132a, 132b, and 132c when they are positioned within the field-of-view of the medical tool 134.

The manipulating system 121 may include a drivable base 122 connected to a telescoping column 124, and one or more manipulator assemblies 126. The manipulator assemblies 126 may include a rotating joint 128 that both rotates and translates parallel to the column 124. The manipulator assemblies 126 may be connected to an orienting platform 129a. The orienting platform 129a may be capable of 360 degrees of rotation. The manipulating system 121 may also include a telescoping horizontal cantilever 129b for moving the orienting platform 129a in a horizontal direction.

In the illustrated embodiment, each of the manipulator assemblies 126 includes a manipulator arm portion 130 that may connect directly to the medical instruments 132a, 132b, and 132c and/or the medical tool 134. The manipulator arm portion 130 may be teleoperatable. The manipulator assemblies 126 may include a manipulator support structure that connects the manipulator arm portion 130 to the orienting platform 129a. Optionally, in some embodiments, the manipulator support structure is not teleoperatable, such that the manipulator support structure may be positioned as desired before the operator O begins operation with the teleoperative components.

Figure 2A:
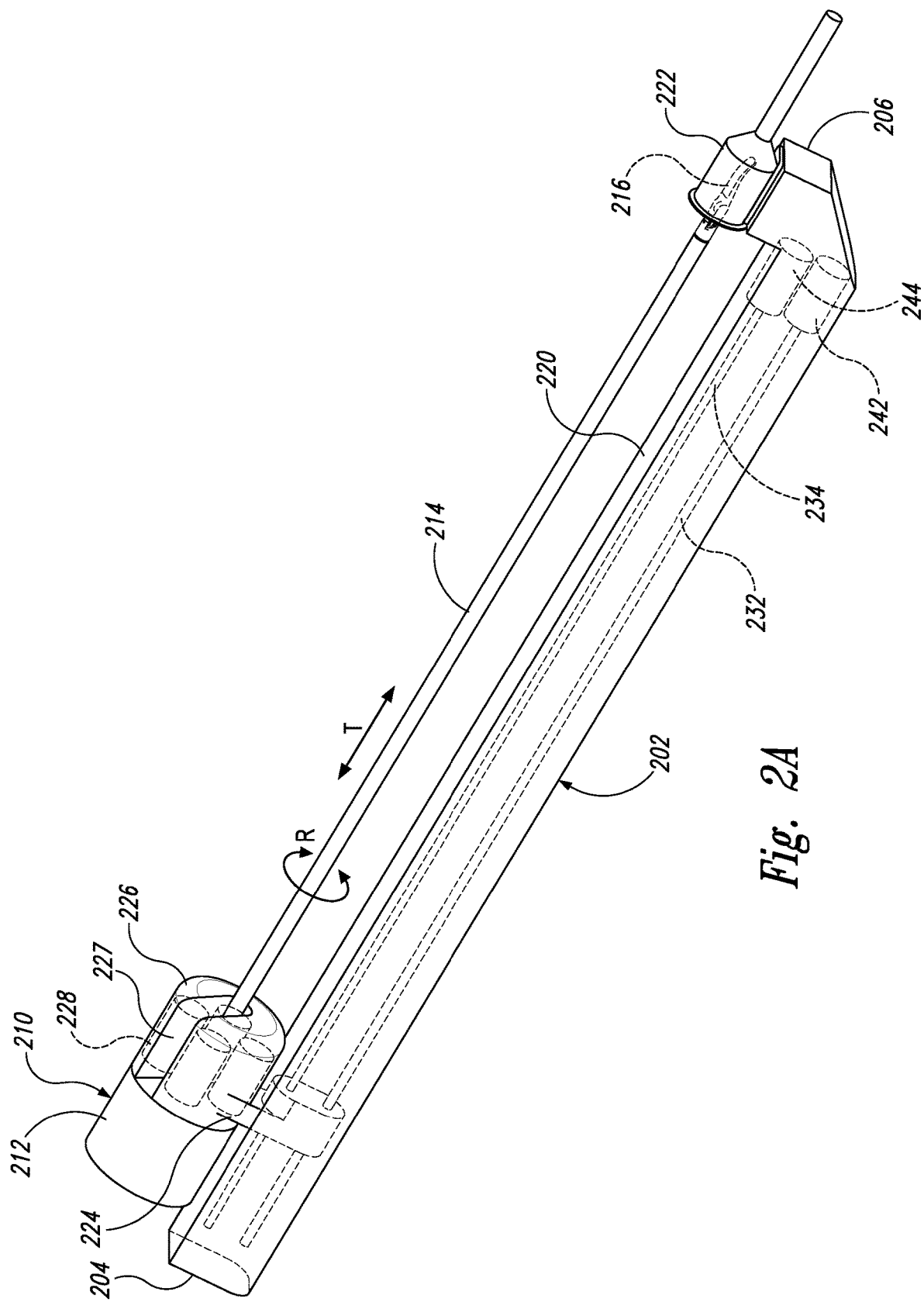
FIGS. 2A and 2B are perspective and right side elevation views, respectively, of an instrument holder and medical instrument assembly configured in accordance with embodiments of the present disclosure.
Figure 2B:
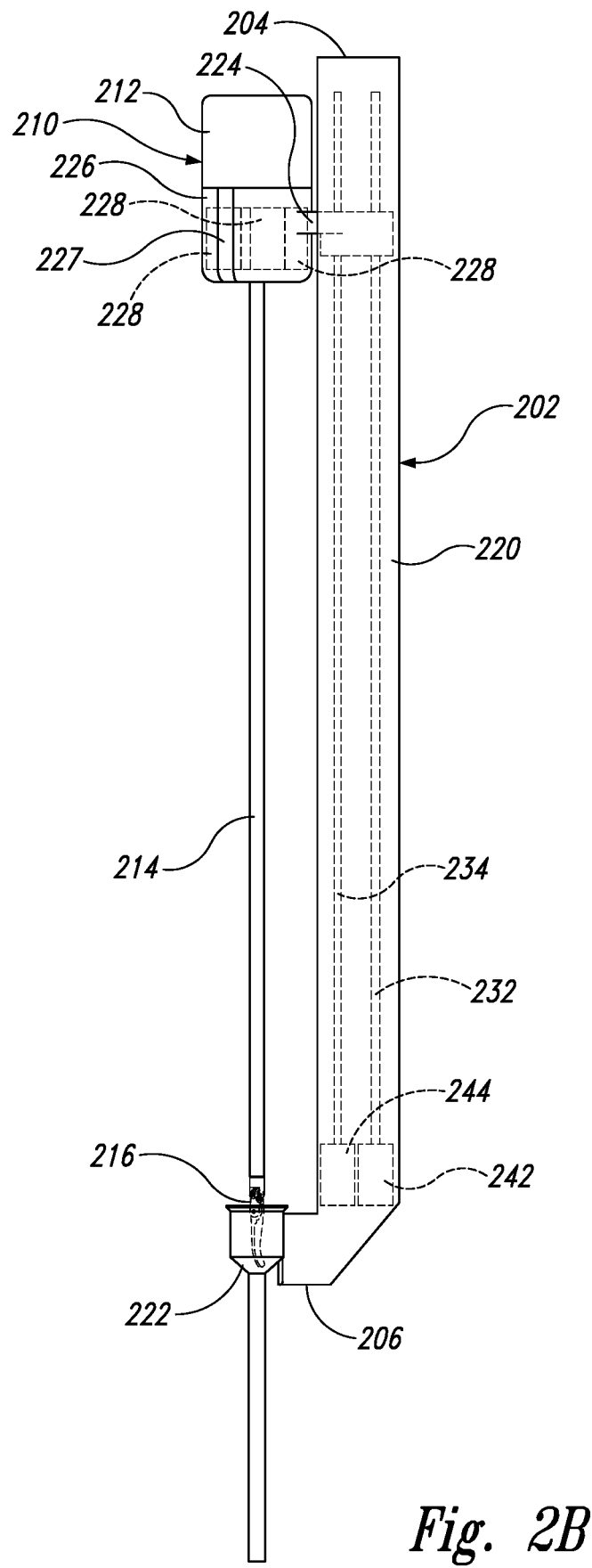

FIGS. 2A and 2B are perspective and right side elevation views, respectively, of an instrument holder 202 and a medical instrument 210 configured in accordance with embodiments of the present disclosure. In some configurations, such as the configuration shown in FIG. 1B, the instrument holder 202 may form part of the manipulator arm portion 130. The medical instrument 210 is generally removably couplable to the instrument holder 202, as will be described in greater detail below. During use, manipulation of the manipulator assemblies 126 can position the instrument holder 202 and medical instrument 210 while the medical instrument 210 is translated, rotated, and/or articulated. The instrument holder 202 may be configured to support and actuate the medical instrument 210 during the medical procedure. The medical instrument 210 may be a therapeutic surgical instrument, an endoscopic camera, etc., and may correspond to the medical instruments 132a, 132b, 132c and/or the medical tool 134 of FIG. 1A. Referring to FIGS. 1A-2B together, the instrument holder 202 and the medical instrument 210 may be controlled using the control system 110 such that the operator O can manipulate the medical instrument 210 during a medical procedure using the user control system 106. The instrument holder 202 and the medical instrument 210 may communicate with the system 100 via various cables and connectors suitable for transferring information (e.g., data signals, light, electrical current, etc.) between them and the system 100 through the control system 110. During a procedure, one or more medical instruments 210 can be positioned in the patient coordinate space 120 in relation to the patient P by mounting the medical instruments 210 to other manipulating systems.

The instrument holder 202 may include an instrument holder base member 220 (which may be an elongate spar) having a proximal end portion 204 and a distal end portion 206. The instrument holder base member 220 may be configured to carry and/or position components of the instrument holder 202 during use of the medical instrument 210, and may include one or more surfaces coupled to more proximal portions of the manipulator arm portion 130 (e.g., via one or more joints). In this regard, the instrument holder base member 220 may have a generally constant cross-section along its length such that the instrument holder 202 may be coupled to a manipulator assembly centrally, or nearer the proximal end portion 204 or the distal end portion 206. In other embodiments, the instrument holder base member 220 may have any suitable cross section along its length, and may include one or more features to assist in positioning the instrument holder 202 with respect to the patient coordinate space (e.g., distance indices, protrusions (not shown), indentations (not shown), etc.). The instrument holder base member 220 may have chambers or internal openings to house components of the instrument holder 202, as will be described in greater detail below. The instrument holder base member 220 may be configured to retain a cannula 222 near the distal end portion 206 for providing an interface between the surgical opening in the patient P and the medical instrument 210 during the medical procedure. The cannula 222 may be removably coupled to the instrument holder base member 220 such that the cannula 222 can be separated from the instrument holder base member 220, e.g., for sterilization.

The instrument holder 202 may further include a carriage support 224 that supports and connects a rotatable carriage 226 to the instrument holder base member 220. The carriage support 224 may be slidingly associated with instrument holder base member 220 to translate the rotatable carriage 226 along the instrument holder base member 220 (e.g., longitudinally). The carriage support 224 may include a portion extending into the instrument holder base member 220 to interface with one or more drive elements configured to control an axial position of the carriage support 224 and rotatable carriage 226 with respect to the instrument holder base member 220, and/or an angular position of the rotatable carriage 226 with respect to the carriage support 224 and the instrument holder base member 220. As shown, the instrument holder 202 may include an axial drive element 242 (e.g., a motor, actuator, etc.) operably coupled to an axial drive shaft 232 to control the axial position of the rotatable carriage 226 with respect to the instrument holder base member 220. The instrument holder 202 may also include a rotational drive element 244 (e.g., a motor, actuator, etc.) operably coupled to a rotational drive shaft 234 to control the angular position of the rotatable carriage 226 with respect to the instrument holder base member 220. The axial and rotational drive shafts 232 and 234 are examples of transmission members that may be used to effectuate axial and/or rotational movement of the rotatable carriage 226. In alternative embodiments, the transmission members controlling the axial and/or angular position of the rotatable carriage 226 may include cables, belts, or any other suitable transmission member. The axial and rotational drive shafts 232 and 234 may extend from the axial and rotational drive elements 242 and 244 to the carriage support 224 for axial positioning of the carriage support 224 and rotatable carriage 226 with respect to the instrument holder base member 220, and angular positioning of the rotatable carriage 226 with respect to the carriage support 224 and the instrument holder base member 220.

In the illustrated configuration of FIGS. 2A and 2B, the axial drive shaft 232 may have threads (not shown) configured to interface with complementary threads (not shown) in the carriage support 224 such that when the axial drive shaft 232 is rotated, the carriage support 224 traverses along (e.g., longitudinally) the instrument holder base member 220 to a different axial position. When a tool is mounted to the carriage 226 and the carriage 226 is translated longitudinally relative to the instrument holder base member 220 in the direction of arrow T, the instrument shaft and end effector will translate in the direction of arrow T along with the carriage (corresponding to the instrument shaft insertion direction). The rotational drive shaft 234 may have features (e.g., gear teeth or splines) to actuate complementary features of the carriage support 224 and/or rotatable carriage 226 such that when the rotational drive shaft 234 is rotated, the rotatable carriage 226 rotates correspondingly with respect to the carriage support 224. When a tool is mounted to the carriage 226 and the carriage is rotated relative to the instrument holder base member in the direction of arrow R, the instrument shaft and end effector will also rotate in the direction of arrow R with the rotation of the carriage. In this configuration, the central axis of rotation of the rotatable carriage 226 coincides with the shaft 214 of the instrument 210. The illustrated embodiments depict a configuration of the instrument holder 202 allowing axial and rotational positioning of the rotatable carriage 226 with respect to the instrument holder base member 220. However, in other embodiments, any number of drive elements may be used with the instrument holder 202 to position the rotatable carriage 226 in any desired position and/or orientation.

The rotatable carriage 226 may have a cylindrical shape and may be rotatably coupled to the carriage support 224 such that the rotatable carriage 226 is manipulable by the axial and rotational drive elements 242 and 244, as described above. The rotatable carriage 226 may be configured to support and mount the medical instrument 210 on a proximal end portion of the rotatable carriage 226 (i.e., away from the surgical site) and transfer actuation forces to the mounted medical instrument 210. An attached medical instrument 210 can be manipulated by the axial and rotational drive elements 242 and 244 for use during a medical procedure wherein actuation forces output by the drive elements 242 and 242 are transferred to the medical instrument 210. In this regard, change(s) in position and orientation of the rotatable carriage 226 generally correspond to the same change(s) in position and orientation of the medical instrument 210. However, portions of the medical instrument 210 may still be individually manipulated independent of the change(s) in position and orientation of the rotatable carriage 226 (e.g., articulation and/or manipulation of an end effector 216, etc.). In the illustrated embodiments, the rotatable carriage 226 is configured to change the axial position and the angular orientation of the medical instrument 210. However, the rotatable carriage 226 may be further configured to change any position and/or orientation of the medical instrument 210.

The rotatable carriage 226 may further include one or more components in mechanical, optical, and/or electrical communication with the distal end portion of the medical instrument 210. As shown, for example, the rotatable carriage 226 may include drive elements 228 (e.g., motors or actuators) arranged within the rotatable carriage 226 to transfer mechanical movement through the proximal end portion of the carriage 226 to the medical instrument 210. For example, the drive elements 228 may be configured to articulate and/or manipulate the end effector 216, among other possible movements. The drive elements 228 may be controlled by electrical signals entering the rotatable carriage 226 from a connector positioned on the rotatable carriage 226, on the medical instrument 210, or passing through the carriage support 224 to the rotatable carriage 226. The drive elements 228 may be connected to output drive couplings of the carriage 226 to transfer articulation forces to the medical instrument 210.

The medical instrument 210 may include an instrument housing 212, a shaft 214, and an end effector 216. The medical instrument 210 may include a plurality of articulable degrees of freedom that can be articulated when mounted to the rotatable carriage 226. The instrument housing 212 is configured to removably couple the medical instrument 210 to the proximal end portion of the rotatable carriage 226 (e.g., a distal end portion of the instrument housing 212 may be coupled to the proximal end portion of the carriage 226). The instrument housing 212 is generally configured to enclose various internal components of the medical instrument 210 (which are omitted from the figures for sake of clarity). The instrument housing 212 may include one or more force transmission input couplings at the distal end portion (e.g., disks, not shown) of the housing 212, wherein the force transmission input couplings correspond to the drive elements 228. Such input couplings may be configured to receive an output from the drive elements 228 of the carriage 226, and thereby cause manipulation of the medical instrument 210. For example, one of the input couplings of the instrument 210 can be used to articulate the end effector 216 of the medical instrument 210 around a first axis (e.g., pitch axis), another input coupling can be used to articulate the end effector 216 around a second axis (e.g., yaw axis) that is perpendicular to the first axis, another input coupling can be used to articulate a clamping jaw of the end effector 216, and another input coupling can be used to articulate a stapling and cutting cartridge of the end effector 216. The medical instrument 210 also may include an instrument shaft 214 extending away from the instrument housing 212 toward the distal end portion 206 of the instrument holder base member 220. The instrument shaft 214 may have the end effector 216 positioned at an end of the instrument shaft 214, and may be configured to enter the patient P through the cannula 222. The instrument shaft 214 may be configured to surround one or more of the internal components of the medical instrument 210 (e.g., cables, wires, fibers, light guides, etc.).

As described above, the rotatable carriage 226 may be rotated relative to the instrument holder base member 220 in the direction of arrow R. As the rotatable carriage 226 rotates, portions or all of the medical instrument 210 mounted to the carriage will also be rotated (e.g., in a direction corresponding to roll of the shaft 214 and the end effector 216). For example, in some embodiments, the rotation of the rotatable carriage 226 will cause the shaft 214 of the instrument to rotate in a roll direction without twisting the shaft 214 relative to other components of the medical instrument 210. In some embodiments, rotation of the carriage may cause the entire instrument to roll as a single unit. The rotation of the medical instrument 210 by the rotatable carriage 226 allows adjustable orientation in the roll degree of freedom (DOF) of the end effector 216 without twisting of the instrument shaft 214 relative to other components of the medical instrument 210. In this regard, the internal components (e.g., wires, cables, fibers, light guides, etc.) of the instrument shaft 214 do not experience the unwrap torque described above, thereby reducing tensile load on the inner wrap and/or core of the internal components of the instrument shaft 214, and extending the life of the medical instrument 210. By rolling the rotatable carriage 226 of the instrument holder 202, the internal friction of the internal components of the instrument shaft 214 is consistent such that articulation of the end effector 216 during use can be more consistently and precisely controlled by an operator O.

Figure 3A:
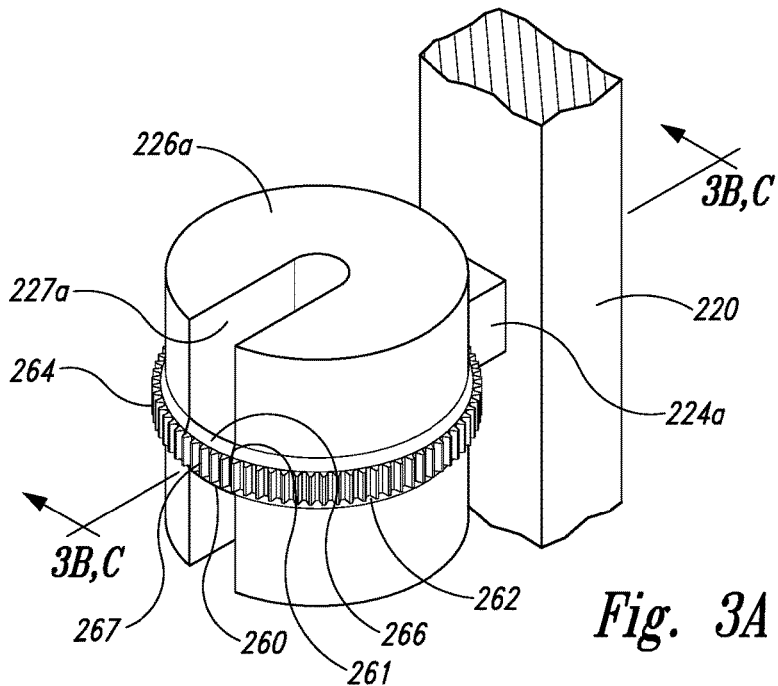
FIG. 3A is a perspective detail view and FIGS. 3B and 3C are top plan detail views of a portion of the instrument holder of FIGS. 2A and 2B, showing a rotatable carriage with a positionable door.
Figure 3B:
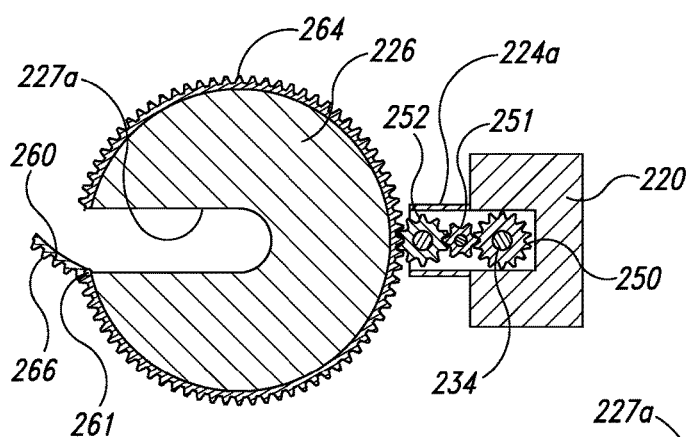
Figure 3C:
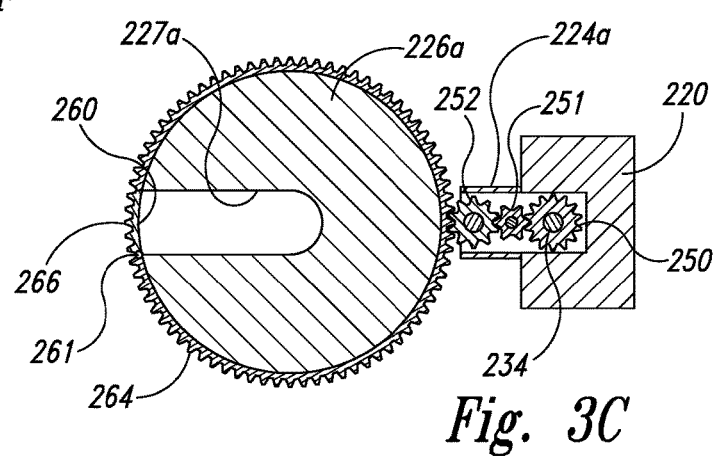

FIG. 3A is a perspective detail view and FIGS. 3B and 3C are top plan detail views of a portion of the instrument holder 202 in accordance with embodiments of the present disclosure. In some embodiments, the medical instrument 210 may be installed to the proximal end portion (opposite from the patient-facing side) of the rotatable carriage 226a by inserting the instrument shaft 214 laterally through an opening (e.g., a slot 227a). The slot 227a extends radially outward from a central axis of the rotatable carriage 226a and from the proximal to distal end portions of the rotatable carriage 226a (see FIG. 3A). Without the slot 227a, installation of the medical instrument 210 on the proximal end of the rotatable carriage 226a may require insertion of the entire shaft 214 of the medical instrument 210 through the rotatable carriage 226a to reach the cannula 206. Installation of the medical instrument 210 in this manner may be difficult because the insertion may need to start from a tall height. To ease installation, the slot 227a of the rotatable carriage 226a instead allows the medical instrument 210 to be installed in a direction lateral to the axis of the shaft 214 (i.e., from the side). For example, in the embodiment of FIGS. 3A-3C, the slot 227a is configured to enable the shaft 214 of the medical instrument 210 to be inserted laterally towards the rotatable carriage 226a. However, the slot 227a may generally limit the possible angular range of motion of the rotatable carriage 226a relative to the instrument holder 202 because the rotatable carriage 226a is connected to the carriage support 224a. For example, the slot 227a may make it such that the slot 227a cannot rotate past the position of the carriage support 224a. As such, the connected medical instrument 210 would have a decreased amount of possible roll ROM.

After installation of the medical instrument 210 to the rotatable carriage 226a, the slot 227a may affect the capability of the instrument holder 202, e.g., limit the range of rotation of the rotatable carriage 226a. In this regard, certain components of the instrument holder 202 and/or the medical instrument 210 may be modified to allow greater rotation of the rotatable carriage 226a with respect to the carriage support 224a. For example, it may be desirable to bridge the slot 227a such that a gear drive engaging an outer surface of the rotatable carriage 226a does not lose contact (see FIGS. 3A-3C), extend a rail guide farther than the slot 227a to maintain contact with the outer surface of the rotatable carriage 226b (see FIGS. 4A and 4B), or otherwise fill the slot 227c, e.g., with a fin extending from the medical instrument 210c (see FIGS. 5A-7B), among other modifications.

The rotatable carriage 226a may be configured such that medical instruments can be coupled on either the proximal or distal end portions of the rotatable carriage 226a. In this regard, a dual instrument configuration (not shown) may include a first instrument installed to the distal end portion of the rotatable carriage, or a second instrument installed to the proximal end portion of the rotatable carriage by inserting the instrument shaft of the second instrument through the slot. For example, the first medical instrument may be an articulating instrument attached to the distal end portion of the rotatable carriage, and the second medical instrument may be an endoscope attached to the proximal end portion of the rotatable carriage and extending through the slot. In these embodiments, either instrument configuration may be controlled by a single instrument holder.

FIG. 3A illustrates the rotatable carriage 226a with a positionable door 260 having a hinge 261 on a first edge of the slot 227a. The positionable door 260 may be configured to rotate between any of a first position (e.g., outwardly open, see FIG. 3B), a second position (e.g., closed, see FIG. 3C), and a third position (e.g., inwardly open, not shown). As shown, the rotatable carriage 226a may include a circumferential track 262 extending around a circumferential outer surface of the rotatable carriage 226a. The circumferential track 262 may be fixed to or removable from the rotatable carriage 226a. The circumferential track 262 may include a positioning member (e.g., "gear teeth 264") configured to be driven by an output drive (e.g., "drive gear 250") (see FIGS. 3B and 3C) positioned within the instrument holder base member 220. The drive gear 250 may be coupled to the rotational drive element 244 (see FIGS. 2A and 2B) through the rotational drive shaft 234. The drive gear 250 may be operably coupled to the gear teeth 264 of the circumferential track 262 through a gear train having any number of drive elements (e.g., gears, belts, worm drives, etc.). Additionally, the drive gear 250 is configured to drive the gear teeth 264 via the gear train. In the illustrated embodiment, the gear train has a first gear 251 and a second gear 252 mechanically coupling the drive gear 250 and the gear teeth 264. In this regard, the rotational drive element 244 may be configured to rotate the rotational drive shaft 234 and the drive gear 250, thereby rotating the rotatable carriage 226a by engaging the gear teeth 264 of the track 262 with the gear train. As the drive gear 250 and gear train rotate the rotatable carriage 226a, the slot 227b rotates toward the carriage support 224a, the drive gear 250, and the gear train. Engagement of the drive gear 250 and gear train with the rotatable carriage 226a can be maintained by bridging the slot 227a with the positionable door 260. In other embodiments, the gear teeth 264 may extend directly from the outer surface of the rotatable carriage 226a, or may be formed by indentations in the outer surface of the rotatable carriage 226a such that the gear teeth 264 do not increase the outer diameter of the rotatable carriage 226a.

In a first position (as shown in FIG. 3B), the positionable door 260 allows the instrument shaft 214 to be inserted into or removed from the slot 227a, e.g., during installation and removal of the medical instrument 210. In a second position (as shown in FIG. 3C), the positionable door 260 may be configured to abut a second edge of the slot 227a to form a bridge across the slot 227a aligned with the track 262. In this regard, the positionable door 260 may include a track section 266 having gear teeth 267 that generally match the track 262 and the gear teeth 264, respectively, creating a continuous loop of gear teeth (244 and 267) to be driven by the drive gear 250 via the gear train. With the positionable door 260 in the second position, as the drive gear 250 and gear train continue to rotate the rotatable carriage 226a such that the slot 227b passes by the drive gear 250 and the gear train during the rotation, the drive gear 250 will be coupled to the gear teeth 267 of the positionable door 260 via the gear train and continue to rotate the rotatable carriage 226a continuously, e.g., >360° in roll ROM. Continuing rotation in this manner will cause the drive gear 250, via the gear train, to again couple with the gear teeth 264 on the other side of the slot 227a. In this second position, the positionable door 260 allows the rotatable carriage 226a to continue to rotate in either direction as the slot 227a passes by the drive gear 250 and gear train, which allows the rotatable carriage 226a to travel through a greater rotation than otherwise possible (e.g., >270° in either direction). In some embodiments, the tracks 262 and 266 are omitted and the gear teeth 264 and 267 are positioned directly on the surface of the rotatable carriage 226a and the positionable door 260, respectively. In further embodiments, the positionable door 260 is coupled near the distal end portion of the rotatable carriage 226a such that a continuous loop of gear teeth is positioned on the distal surface of the rotatable carriage 226a similar to the gear teeth shown in FIG. 6B.

In some embodiments, the positionable door 260 may default to the second position, for example, via a spring that biases the positionable door 260 toward the second position. The positionable door 2006 may therefore be allowed to rotate in either direction on the hinge 261, e.g., inward toward the central axis of the rotatable carriage 226a upon insertion of the instrument shaft 214, and outward (as shown) during removal of the instrument shaft 214 from the slot 227a, and automatically return back to the second position. In some embodiments, a lock mechanism (not shown) may be included to fix the positionable door 260 at the second position until the lock mechanism is disabled.

Figure 4A:
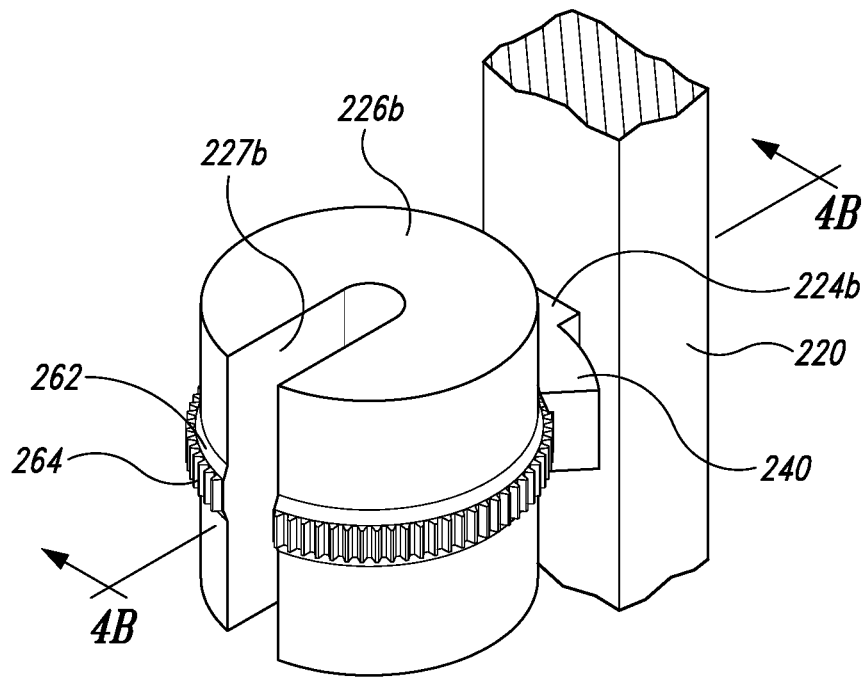
FIG. 4A is a perspective detail view and FIG. 4B is a top plan detail view of a portion of the instrument holder of FIGS. 2A and 2B, showing curved track guides extending from a carriage support.
Figure 4B:
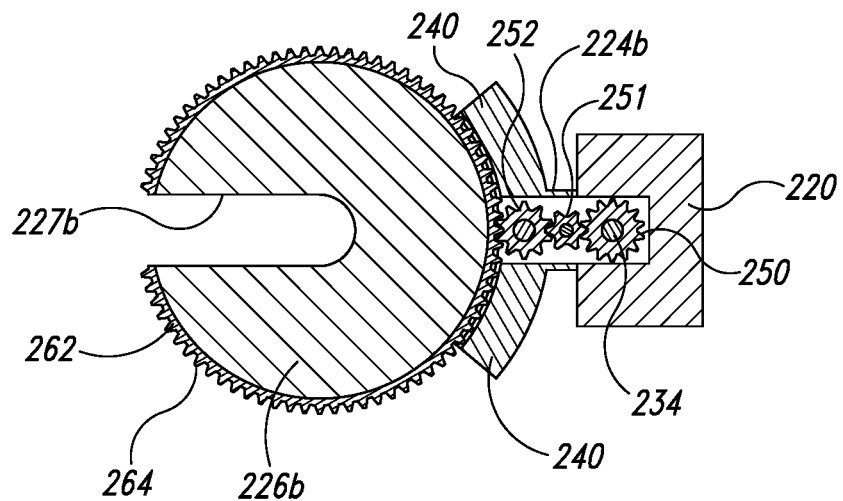

FIG. 4A is a perspective detail view and FIG. 4B is a top plan detail view of a portion of the instrument holder 202 in accordance with embodiments of the present disclosure, showing curved track guides 240 extending from the carriage support 224b. The curved track guides 240 may be configured to project away from the carriage support 224b and project circumferentially along the surface of the rotatable carriage 226b. The curved track guides 240 may be aligned with the track 262 such that as the rotatable carriage 226b is rotated, the track 262 travels through the curved track guides 240. The track 262 and/or curved track guides 240 may include features (e.g., a slot, protrusion, etc., not shown) to engage with each other and retain the rotatable carriage 226b against the curved track guides 240 and carriage support 224b. As shown, the slot 227b forms a gap in the track 262 and interrupts the engagement of the carriage support 224b with the track 262 and the drive gear 250, the first gear 251, and the second gear 252 with the gear teeth 264. Without the curved track guides 240, the rotation of the rotatable carriage 226b would be limited to the engagement of the track 262 with the carriage support 224b, and may have less rotation than desired for certain medical procedures. In this regard, the rotation of the rotatable carriage 226b could be limited before the drive gear 250 and gear train couple to the gear teeth 264 positioned near the slot 227b.

To increase the rotation capability of the rotatable carriage 226b, the curved track guides 240 may have an arc length longer than a width of the slot 227b and configured to extend across the slot 227b to engage a portion of the track 262 on the opposite side of the slot 227b. The engagement of the track 262 across the slot 227b by the curved track guides 240 allows the rotatable carriage 226b to rotate to an orientation where the drive gear 250 and gear train couple to the gear teeth 264 immediately adjacent the slot 227b, which allows the rotatable carriage 226b to travel through a greater rotation than otherwise possible (e.g., >270° in either direction). In other embodiments, the track 262 and the gear teeth 264 are positioned on the distal surface of the rotatable carriage 226b such that the diameter of the rotatable carriage 226b is no larger than the diameter of the instrument housing 212 (see, e.g., the gear teeth location of FIGS. 6A and 6B).

In these embodiments, the curved track guides 240 may be positioned adjacent the distal end portion of the rotatable carriage 226b to engage the track 262.

Figure 5A:
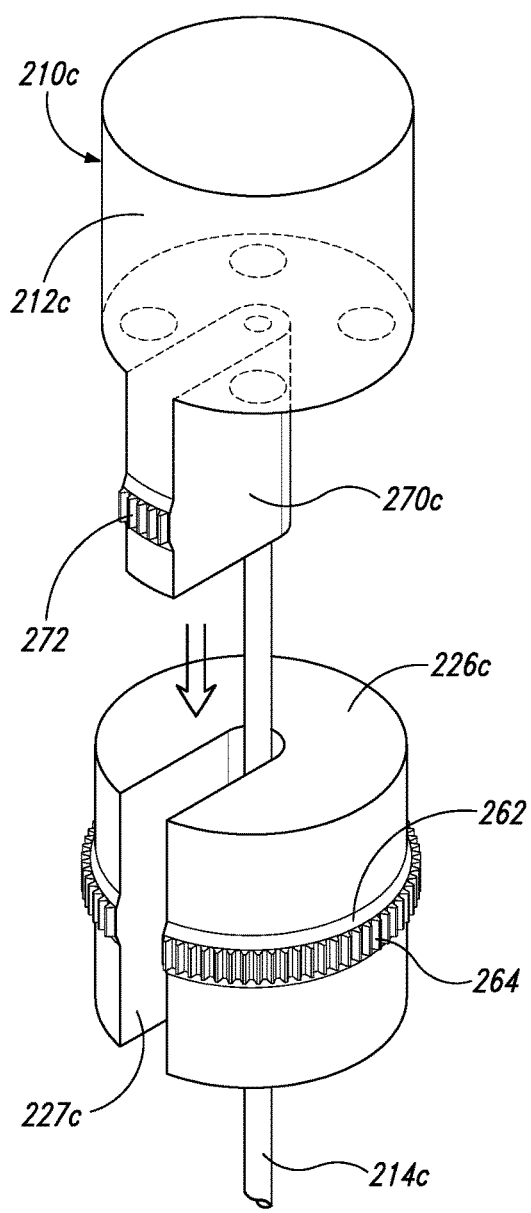
FIGS. 5A and 5B are perspective detail views of a portion of the instrument holder and medical instrument assembly of FIGS. 2A and 2B, showing a rotatable carriage and a medical instrument in a disassembled configuration (FIG. 5A) and an assembled configuration (FIG. 5B).
Figure 5B:
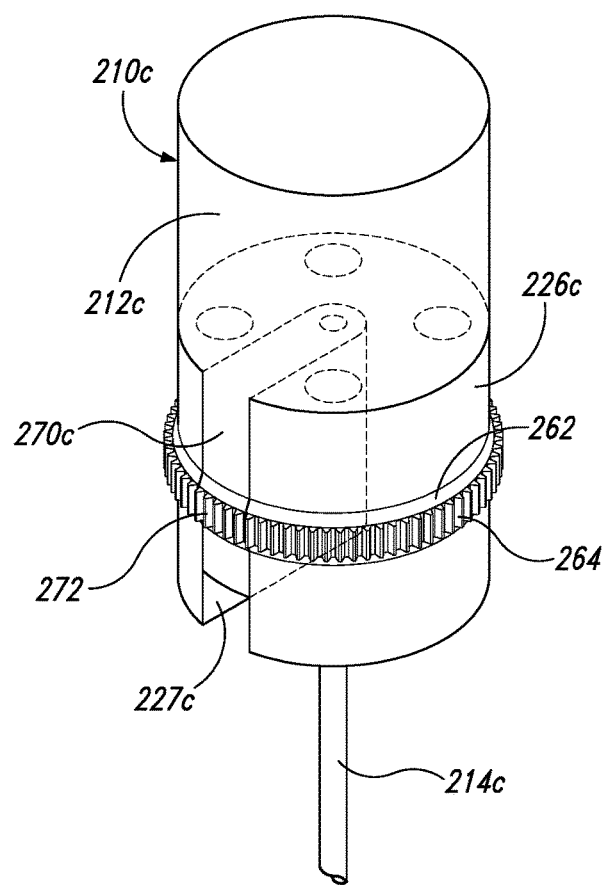

FIGS. 5A and 5B are perspective detail views of a portion of a rotatable carriage 226c and a medical instrument 210c in accordance with embodiments of the present disclosure. In particular, FIG. 5A illustrates the rotatable carriage 226c and the medical instrument 210c in a disassembled configuration, and FIG. 5B illustrates the rotatable carriage 226c and the medical instrument 210c in an assembled configuration. The instrument housing 212c may include a fin 270c projecting away from the distal end portion of the instrument housing 212c in the direction of the instrument shaft 214c. The fin 270c may be fixed to or removable from the instrument housing 212c. The fin 270c may be sized and configured to be inserted into the slot 227c of the rotatable carriage 226c during installation of the medical instrument 210c to the rotatable carriage 226c. The fin 270c may include gear teeth 272 configured to be coupled to the drive gear 250 (e.g., via the gear train). As shown in FIG. 5B, when the medical instrument 210c is in the assembled configuration, the gear teeth 272 may be generally aligned with the gear teeth 264 of the circumferential track 262. In this regard, the fin 270c may be configured to bridge the gap of the slot 227c and extend the gear teeth around the full circumference of the rotatable carriage 226c, allowing the rotatable carriage 226c to continue to rotate in either direction as the slot 227c passes by the drive gear 250 and the gear train, thereby traveling through a greater rotation than otherwise possible (e.g., >360° in roll ROM).

The interface of the fin 270c with the slot 227c may also provide a clocking alignment of the medical instrument 210c during installation to the rotatable carriage 226c. In these embodiments, the distal and of the fin 270c may include rounded surfaces to aid in alignment of the fin 270c with the slot 227c during installation of the medical instrument 210c. The fin 270c also may be configured to increase the housing volume of the medical instrument 210c, allowing more space for internal components.

Figure 6A:
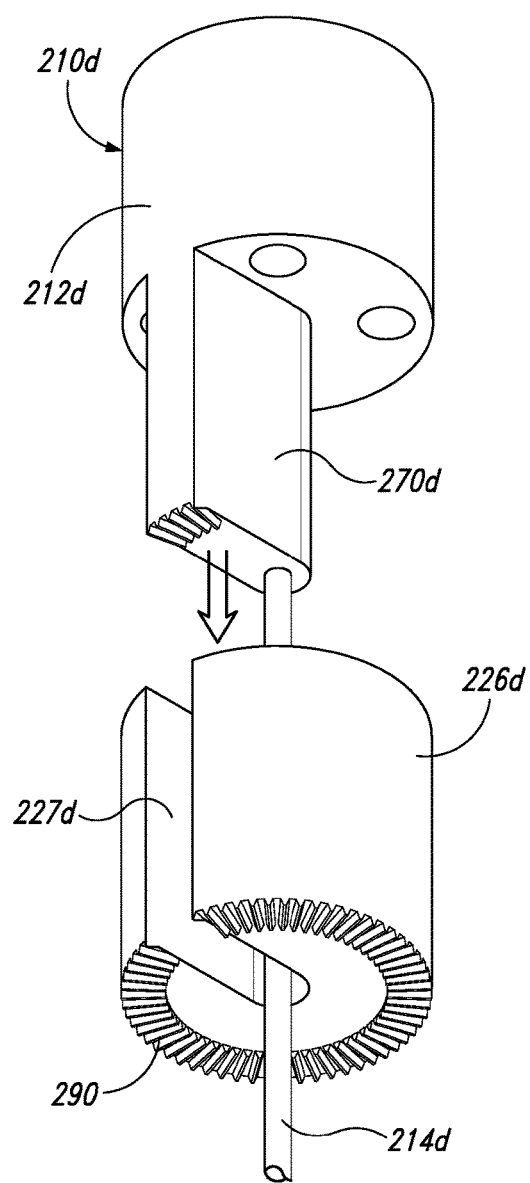
FIGS. 6A and 6B are perspective detail views of a portion of the instrument holder and medical instrument assembly of FIGS. 2A and 2B, showing a rotatable carriage and a medical instrument in a disassembled configuration (FIG. 6A) and an assembled configuration (FIG. 6B).
Figure 6B:
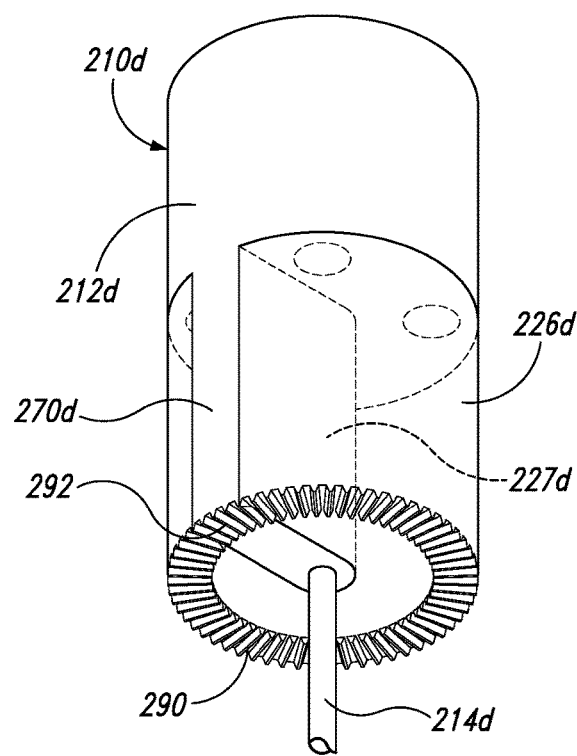

FIGS. 6A and 6B are perspective detail views of a portion of a rotatable carriage 226d and a medical instrument 210d configured in accordance with embodiments of the present disclosure. In particular, FIG. 6A illustrates the rotatable carriage 226d and the medical instrument 210d in a disassembled configuration, and FIG. 6B illustrates the rotatable carriage 226d and the medical instrument 210d in an assembled configuration. The embodiment shown in FIGS. 6A and 6B are similar to the embodiments of FIGS. 5A and 5B described above, except that the rotatable carriage 226d has gear teeth 290 positioned on the distal end portion of the rotatable carriage 226d, and the fin 270d has gear teeth 292 positioned on a distal tip of the fin 270d. As shown, the fin 270d may extend to fill the entire height of the slot 227d such that the distal tip of the fin 270d is generally flush with the distal end portion of the rotatable carriage 226d. As shown in FIG. 6B, when the medical instrument 210d is in the assembled configuration, the gear teeth 292 may be generally aligned with the gear teeth 290 of the rotatable carriage 226d. In this regard, the fin 270d may be configured to bridge the gap of the slot 227d and extend the gear teeth around the full circumference of the distal end portion of the rotatable carriage 226d, allowing the rotatable carriage 226d to continue to rotate in either direction as the slot 227d passes by the drive gear 250 and the gear train, thereby traveling through a greater rotation than otherwise possible (e.g., >360° in roll ROM).

FIGS. 7A and 7B are perspective detail views of a portion of a rotatable carriage 226e and a medical instrument 210e configured in accordance with embodiments of the present disclosure. In particular, FIG. 7A illustrates the rotatable carriage 226e and the medical instrument 210e in a disassembled configuration, and FIG. 7B illustrates the rotatable carriage 226e and the medical instrument 210e in an assembled configuration. The embodiment shown in FIGS. 7A and 7B are similar to the embodiments of FIGS. 5A and 5B described above, except that the rotatable carriage 226e has a groove 280 extending circumferentially around the outer surface of the rotatable carriage 226e, and the fin 270e has a groove 282 generally aligned with the groove 280 in the assembled configuration. In this regard, the fin 270e may be configured to bridge the gap of the slot 227e and extend the groove (by connecting grooves 280 and 282) around the full circumference of the rotatable carriage 226e. In these embodiments, the rotation of the rotatable carriage 226e may be caused by pulling one or more cables (not shown) extending from the carriage support 224e around the rotatable carriage 226e within the grooves 280 and 282. In embodiments where two cables are used (e.g., one cable for clockwise rotation and another cable for counterclockwise rotation), the fin 270e and the groove 282 provide a consistent diameter around the circumference of the rotatable carriage 226e during rotation of the rotatable carriage 226e, thereby allowing travel through a greater rotation than otherwise possible (e.g., >360° in roll ROM).

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present disclosure. Thus, the appearances of such phrases or formulations herein are not necessarily all referring to the same embodiment.

For ease of reference, identical reference numbers are used to identify similar or analogous components or features throughout this disclosure, but the use of the same reference number does not imply that the features should be construed to be identical. Indeed, in many examples described herein, identically numbered features have a plurality of embodiments that are distinct in structure and/or function from each other. Furthermore, the same shading may be used to indicate materials in cross section that can be compositionally similar, but the use of the same shading does not imply that the materials should be construed to be identical unless specifically noted herein.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. An apparatus, comprising:
   a carriage support having an output drive;
   a carriage configured to removably couple an instrument thereto, wherein the carriage has a lateral opening extending radially outward from a central axis of the carriage and extending between a proximal end portion and a distal end portion of the carriage, and wherein the lateral opening is configured to receive a portion of the instrument therein; and
   a positioning member disposed on an outer surface of the carriage and operably coupled with the output drive such that rotation of the output drive changes an angular position of the carriage relative to the carriage support,
   wherein the positioning member is configured to operably couple with the output drive through a range of rotation of the carriage such that a section of the carriage including the lateral opening is rotatable past the output drive, and
   wherein the carriage houses one or more drive elements configured to transmit mechanical force to the instrument in a coupled state of the instrument with the carriage, wherein the one or more drive elements are driven in response to electrical signal communication with the one or more drive elements.

2. The apparatus of claim 1,
   wherein the carriage support is configured to translate the carriage along an instrument holder base member of an instrument holder.

3. The apparatus of claim 2, further comprising:
   an axial drive element operably coupled to an axial transmission member extending to the carriage support; and
   a rotational drive element operably coupled to a rotational transmission member extending to the carriage support,
   wherein the axial drive element is configured to axially position the carriage support with respect to the instrument holder base member, and
   wherein the rotational drive element is configured to angularly position the carriage with respect to the carriage support by rotating the output drive.

4. The apparatus of claim 3, wherein at least one of the axial transmission member or the rotational transmission member is a drive shaft, a belt, or a cable.

5. The apparatus of claim 1, wherein rotation of the carriage causes a shaft roll of the instrument when coupled to the carriage.

6. The apparatus of claim 1, wherein the output drive comprises gear teeth.

7. The apparatus of claim 1, wherein the positioning member comprises gear teeth circumferentially arranged along the outer surface of the carriage.

8. The apparatus of claim 7, wherein the gear teeth of the positioning member are circumferentially arranged along a distal end surface of the carriage.

9. The apparatus of claim 7, wherein the gear teeth of the positioning member are circumferentially arranged along the outer surface of the carriage between the proximal end portion and the distal end portion of the carriage.

10. The apparatus of claim 7,
further comprising a positionable door rotatably coupled to a first edge of the lateral opening,
wherein the positionable door is rotatably movable between a first position wherein the positionable door allows a shaft of the instrument to enter the lateral opening, and a second position wherein the positionable door abuts a second edge of the lateral opening opposite the first edge.

11. The apparatus of claim 10, wherein the positionable door comprises additional gear teeth that align with the gear teeth of the positioning member in the second position of the positionable door to form a continuous loop of the gear teeth and the additional gear teeth around the carriage such that the output drive of the carriage support is operably coupleable with the carriage around an entire circumference of the carriage.

12. The apparatus of claim 10, wherein:
the positionable door projects outward from the outer surface of the carriage in the first position, and
the positionable door is further rotatably movable to a third position wherein the positionable door projects into the lateral opening of the carriage.

13. The apparatus of claim 10, wherein the positionable door has a lock to fix the positionable door in the second position.

14. The apparatus of claim 7, wherein:
the gear teeth of the positioning member are positioned on a track extending around the outer surface of the carriage,
the carriage support further comprises a curved track guide extending away from the output drive, and
the curved track guide is configured to interface with the track of the carriage to support the carriage as the output drive changes the angular position of the carriage.

15. The apparatus of claim 14, wherein an arc length of the curved track guide is longer than a width of the lateral opening such that the curved track guide is configured to extend across the lateral opening and engage with a portion of the track on an opposite side of the lateral opening.

16. The apparatus of claim 7, further comprising the instrument, wherein the positioning member comprises a portion projecting from the instrument, and wherein the lateral opening is configured to receive the portion.

17. The apparatus of claim 16, wherein the portion comprises additional gear teeth that align with the gear teeth of the positioning member when the instrument is coupled to the carriage, and wherein the additional gear teeth of the portion and the gear teeth of the positioning member form a continuous loop around the carriage such that the output drive can engage with the carriage around an entire circumference of the carriage.

18. The apparatus of claim 1, wherein the positioning member is removable from the carriage.

19. The apparatus of claim 1, wherein a proximal surface of the carriage is configured to couple a distal end portion of an instrument housing with an instrument shaft extending through the lateral opening.

20. The apparatus of claim 1, wherein the carriage further comprises one or more drive output couplings configured to releasably couple and transmit drive actuation force to control movement of one or more components of the instrument relative to the carriage in the coupled state of the instrument with the carriage.

21. A manipulator arm for controlling movement of an instrument, the manipulator arm comprising:
a plurality of links coupled by one or more joints; and
an instrument holder configured to couple the one or more joints and plurality of links to the instrument,
wherein the instrument holder comprises:
a base member,
a carriage configured to releasably attach to the instrument and drive the instrument, wherein the carriage comprises a central axis and a lateral opening extending radially outward from central axis, the lateral opening configured to receive a portion of the instrument from external the carriage along a direction substantially perpendicular to the central axis, and
a positioning member positionable adjacent the lateral opening such that the carriage is rotatable with respect to the base member about the central axis to an angular extent such that the lateral opening is configured to rotate past the base member,
wherein the carriage houses one or more drive elements configured to transmit mechanical force to the instrument in a coupled state of the instrument with the carriage, wherein the one or more drive elements are driven in response to electrical signal communication with the one or more drive elements.

22. The manipulator arm of claim 21, wherein the carriage further comprises one or more drive output couplings configured to releasably couple and transmit drive actuation force to control movement of one or more components of the instrument relative to the carriage in the coupled state of the instrument with the carriage.

* * * * *